United States Patent [19]

Doran et al.

[11] Patent Number: 5,428,029
[45] Date of Patent: Jun. 27, 1995

[54] VITAMIN D3 FLUORINATED ANALOGS

[75] Inventors: Thomas I. Doran, West Orange; Bernard M. Hennessy, Nutley, both of N.J.; John A. McLane, West Haven, Conn.; Giacomo Pizzolato, Glen Ridge, N.J.; Farhad Sedarati, Wayne, N.J.; Milan R. Uskokovic, Upper Montclair, N.J.

[73] Assignee: Hoffmann-La Roche Inc., Nutley, N.J.

[21] Appl. No.: 158,068

[22] Filed: Nov. 24, 1993

[51] Int. Cl.⁶ ........................................... C07C 401/00
[52] U.S. Cl. ..................................... 514/167; 552/653
[58] Field of Search ......................... 552/653; 514/167

[56] References Cited

U.S. PATENT DOCUMENTS

| | | | |
|---|---|---|---|
| 4,248,791 | 2/1981 | DeLuca | 552/653 |
| 4,358,406 | 11/1982 | DeLuca et al. | 552/653 |
| 4,613,594 | 9/1986 | Baggiolini et al. | 552/653 |
| 4,804,502 | 2/1989 | Baggiolini et al. | 552/653 |
| 5,087,619 | 5/1992 | Yamada et al. | 552/653 |
| 5,116,573 | 2/1992 | Baggioline et al. | 552/653 |
| 5,145,846 | 9/1992 | Baggioline et al. | 552/653 |
| 5,281,731 | 1/1994 | Deluca et al. | 552/653 |

OTHER PUBLICATIONS

Pinder, et al., *J. Pharm. Sci*, vol. 56 (8) (1967), pp. 970–973.
Farach-Carson et al., Endocrinology 129:1876–1884 (1991).
Zhou et al., Blood 78:75–82 (1991).
Shiuey et al., J. Org. Chem. 55:243–247 (1990).
Kiegiel et al., Tetrahedron Letters 32:6057–6060 (1991).

*Primary Examiner*—Johann Richter
*Assistant Examiner*—Kimberly J. Kestler
*Attorney, Agent, or Firm*—George M. Gould; George W. Johnston; Robert A. Silverman

[57] ABSTRACT

Compounds of the formula

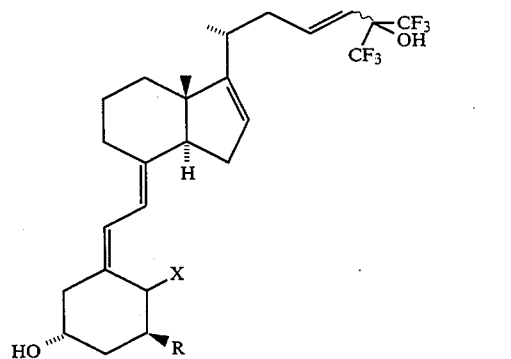

wherein R is hydrogen, hydroxy, or fluorine, X is $H_2$ or $=CH_2$, and the 23,24-double bond is E or Z, are useful as agents for the treatment of hyperproliferative disorders of the skin such as psoriasis, as agents for the treatment of tumors such as breast cancer, as agents for the treatment of neoplastic diseases such as leukemia, and as agents for the treatment of sebaceous gland diseases such as acne and seborrheic dermatitis.

14 Claims, No Drawings

VITAMIN D3 FLUORINATED ANALOGS

BRIEF SUMMARY OF THE INVENTION

The invention relates to compounds of the formula

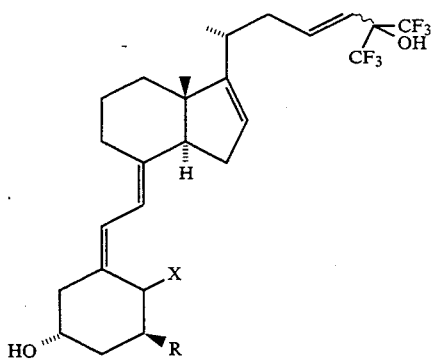

wherein R is hydrogen, hydroxy or fluorine, X is $H_2$ or $=CH_2$ and the 23,24-double bond is E or Z.

Compounds of formula I as described above are useful as agents for the treatment of hyperproliferative skin diseases such as psoriasis. Compounds of formula I as described above are also useful as agents for the treatment and prevention of neoplastic, diseases, such as leukemia, and for the treatment and prevention of tumors. Compounds of formula I above are also useful as agents for the treatment of sebaceous gland diseases, such as, acne and seborrheic dermatitis.

DETAILED DESCRIPTION OF THE INVENTION

In the formulas presented herein, the various substituents are illustrated as joined to the nucleus by one of the following notations: a wedged solid line (⬛) indicating a substituent which is above the plane of the molecule, and a wedged dotted line ( ⁞⁞⁞⁞⁞ ) indicating a substituent which is below the plane of the molecule.

The invention relates to compounds of the formula

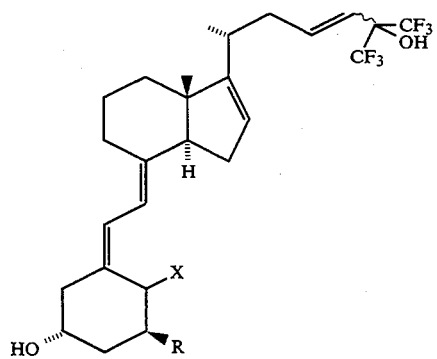

wherein R is hydrogen, hydroxy or fluorine, X is $H_2$ or $=CH_2$ and the 23,24-double bond is E or Z.

Compounds of formula I as described above are highly potent in stimulating differentiation and decreasing proliferation of human keratinocytes. Accordingly, compounds of formula I as described above are useful as agents in the treatment of hyperproliferative skin disorders such as psoriasis, basal cell carcinomas, disorders of keratinization, and keratosis. The compounds of formula I are also useful as agents in the prevention and treatment of neoplastic diseases such as leukemia. In addition, the compounds of formula I are antitumor agents, capable of treating and preventing tumors, such as breast tumors. The compounds of formula I are also useful for the treatment of sebaceous gland diseases, such as, acne and seborrheic dermatitis.

The invention also relates to a pharmaceutical composition comprising an effective amount of a compound of formula I, or an effective amount of a mixture of two or more compounds of formula I.

The invention also relates to a method for treating the above-mentioned disease states by administering to a host in need of such treatment an effective amount of a compound of formula I, or an effective amount of a mixture of two or more compounds of formula I.

Exemplary compounds of formula I of the invention are:
26,26,26,27,27,27-hexafluoro-1α,25-dihydroxy-16,23E-diene-cholecalciferol;
26,26,26,27,27,27-hexafluoro-25-hydroxy-16,23E-diene-cholecalciferol;
26,26,26,27,27,27-hexafluoro-1α-fluoro-25-hydroxy-16,23E-diene-cholecalciferol;
26,26,26,27,27,27-hexafluoro-1α,25-dihydroxy-16,23E-diene-19-nor-cholecalciferol;
26,26,26,27,27,27-hexafluoro-1α,25-dihydroxy-16,23Z-diene-cholecalciferol;
26,26,26,27,27,27-hexafluoro-25-hydroxy-16,23Z-diene-cholecalciferol;
26,26,26,27,27,27-hexafluoro-1α-fluoro-25-hydroxy-16,23Z-diene-cholecalciferol;
26,26,26,27,27,27-hexafluoro-1α,25-dihydroxy-16,23Z-diene-19-nor-cholecalciferol;

In the compound of formula I, R is preferably hydroxy or fluorine.

Preferred compounds of formula I are:
26,26,26,27,27,27-hexafluoro-1α,25-dihydroxy-16,23E-diene-cholecalciferol;
26,26,26,27,27,27-hexafluoro-1α-fluoro-25-hydroxy-16,23E-diene-cholecalciferol; and
26,26,26,27,27,27-hexafluoro-1α,25-dihydroxy-16,23E-diene-19-nor cholecalciferol.

The compounds of formula I are prepared as hereafter described, with particular reference to the Formula Schemes below.

SCHEME 1
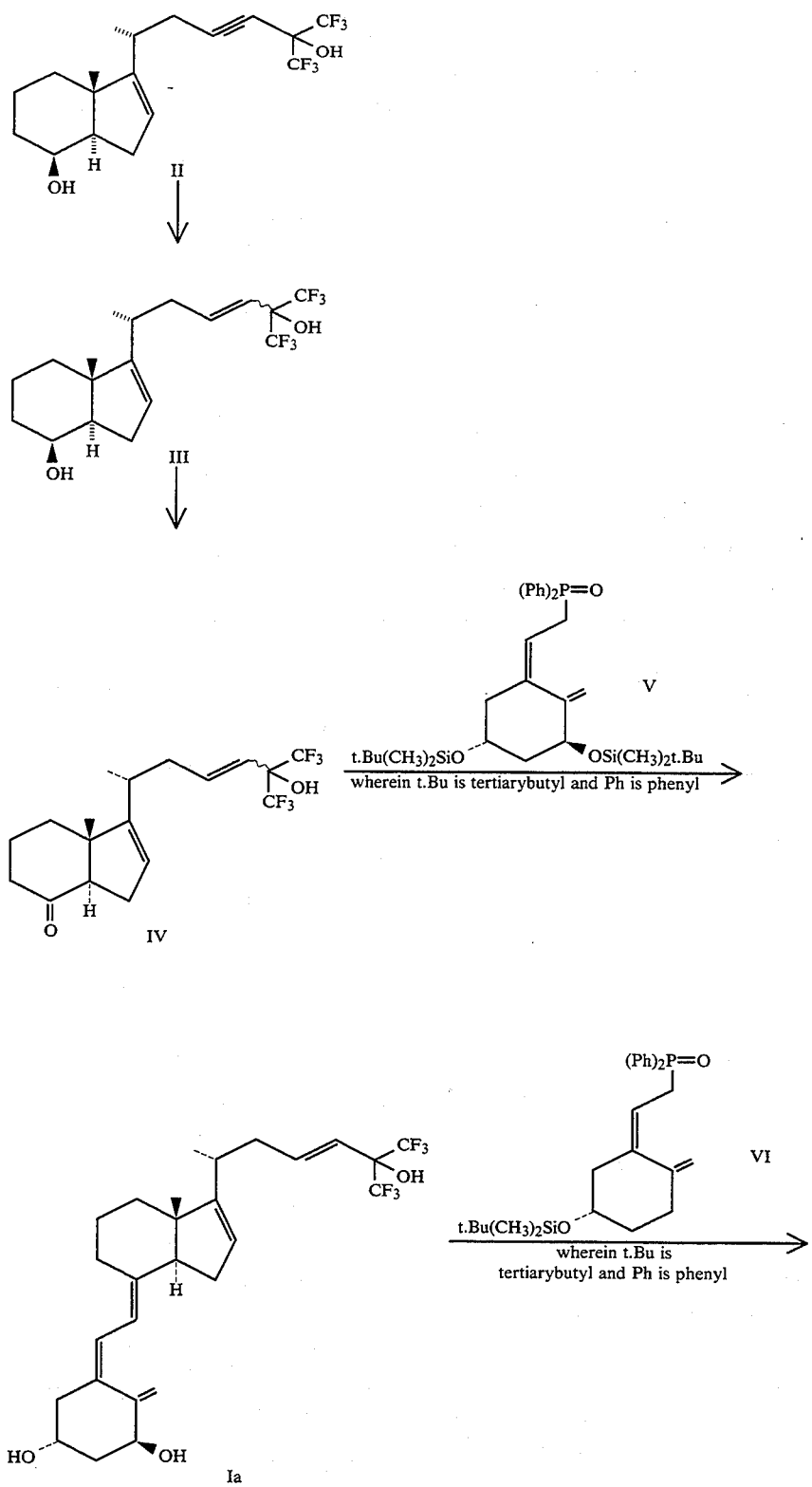

SCHEME 1

-continued

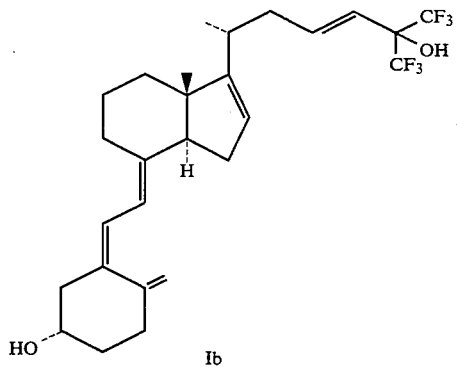

In above Formula Scheme I, the compound of formula II, a known compound, is converted to the trans analog of the compound of formula III by reaction with a reducing agent such as lithium aluminum hydride in the presence of a base, such as sodium methoxide. The reaction is conducted in an ether solvent such as tetrahydrofuran at about 0° C. to about 100° C. The compound of formula II is converted to the cis analog of the compound of formula III by hydrogenation with Lindlar catalyst in the solvent mixture of ethyl acetate, hexane and ethanol.

The cis or trans analog of the compound of formula III is reacted with pyridinium chlorochromate in a chlorinated hydrocarbon solvent such as methylene chloride at room temperature to give the cis or trans analog of the compound of formula IV, respectively.

The trans analog of the compound of formula IV is reacted with n-butyllithium and the compound of formula V in a mixture of hexane and tetrahydrofuran at a temperature of −75° C. to give a compound of formula Ia, a trans compound, after removal of silyl protecting groups with tetrabutylammonium fluoride in tetrahydrofuran solvent.

The trans analog of the compound of formula IV is reacted with n-butyllithium and the compound of formula VI in a mixture of hexane and tetrahydrofuran, at a temperature of −75° C. to give the compound of formula Ib, a trans compound, after removal of the silyl protecting group with tetrabutylammonium fluoride in tetrahydrofuran solvent.

SCHEME II

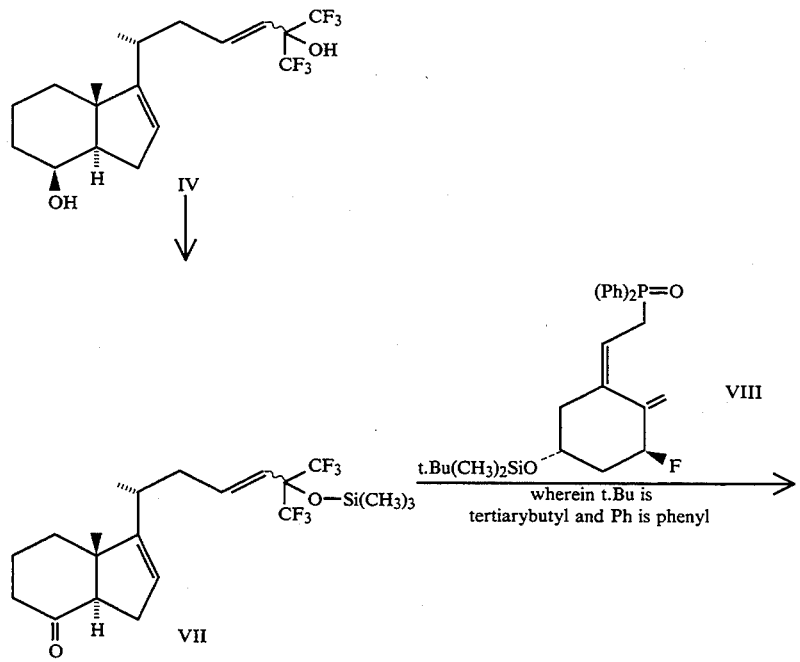

SCHEME II

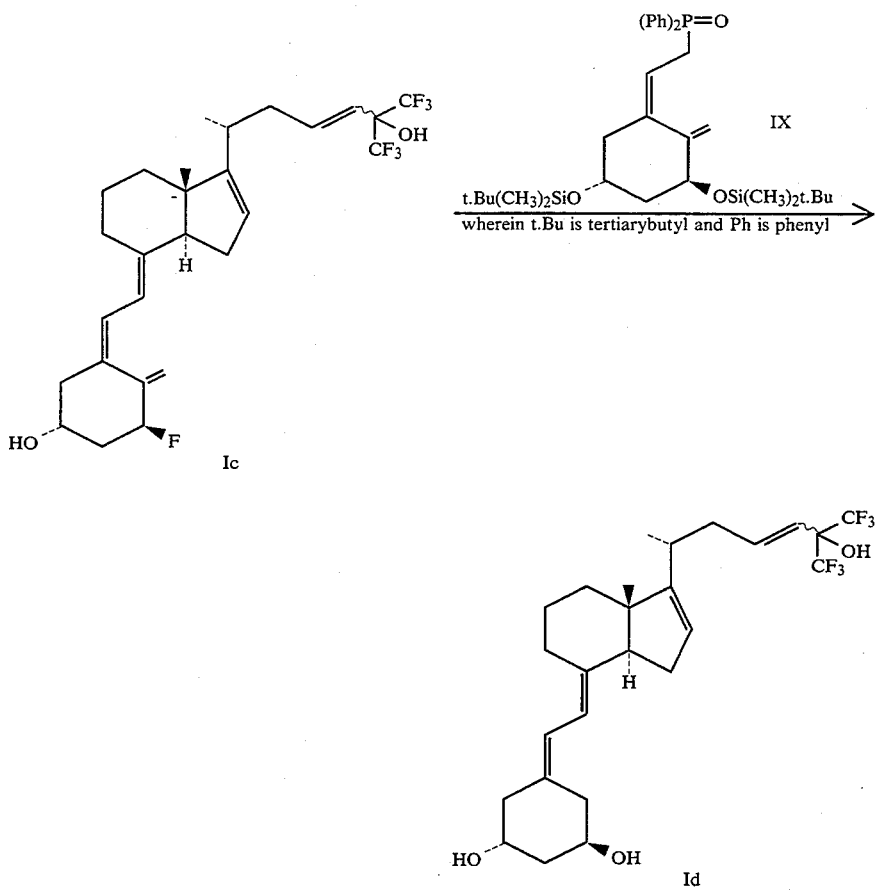

In formula Scheme II, the compound of formula IV, in which the 23,24 double bond is either E or Z, is reacted with trimethylsilyl imidazole in methylene chloride at room temperature to give the compound of formula VII, in which the 23,24 double bond is either E or Z, respectively.

The cis or trans compound of formula VII is reacted with n-butyllithium and the compound of formula VIII, a known compound, in a mixture of hexane and tetrahydrofuran solvent at a temperature of −75° C. to give the cis or trans compound of formula Ic, respectively, after removal of the silyl protecting group with tetrabutylammonium fluoride in tetrahydrofuran solvent.

The cis or trans compound of formula VII is reacted with n-butyllithium and the compound of formula IX, a known compound, in a mixture of hexane and tetrahydrofuran solvent at a temperature of −75° C. to give the cis or trans compound of formula Id, respectively, after removal of the silyl protecting group with tetrabutylammonium fluoride in tetrahydrofuran solvent.

SCHEME III

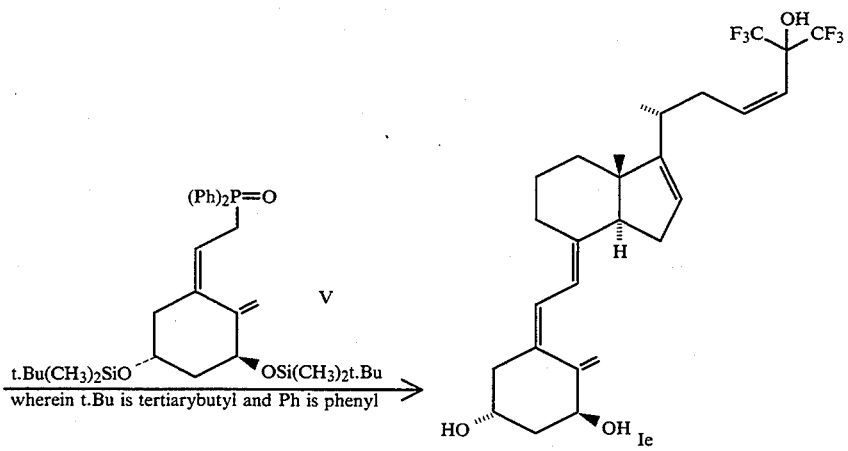

-continued
SCHEME III

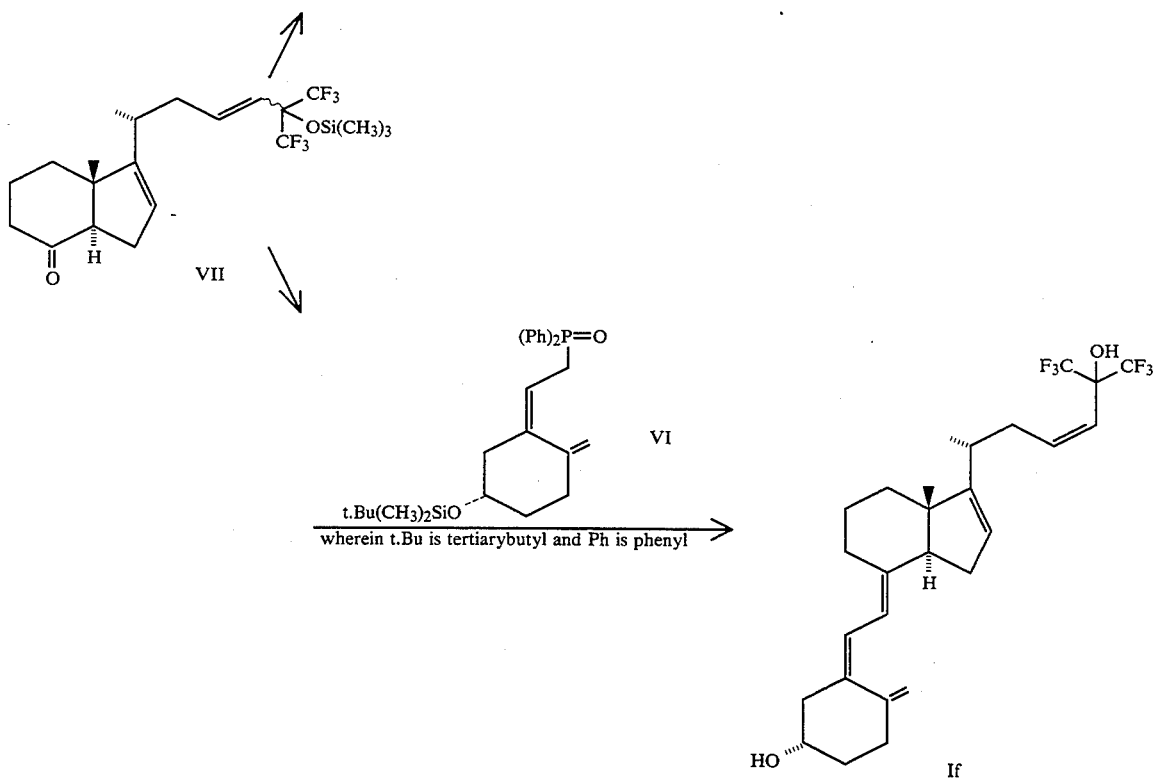

wherein t.Bu is tertiarybutyl and Ph is phenyl

In Formula Scheme III, the cis analog of the compound of formula VII is reacted with n-butyllithium and the compound of formula V in a mixture of hexane and tetrahydrofuran solvent at a temperature of −75° C. to give the compound of formula Ie, the cis analog of the compound of formula Ia, after removal of the silyl protecting groups with tetrabutylammonium fluoride in tetrahydrofuran solvent.

The cis analog of the compound of formula VII is reacted with n-butyllithium and the compound of formula VI in a mixture of hexane and tetrahydrofuran solvent at a temperature of −75° C. to give the compound of formula If, the cis analog of the compound of formula Ib, after removal of the silyl protecting groups with tetrabutylammonium fluoride in tetrahydrofuran solvent.

The compounds of formula I as described above can be administered orally, for the treatment of neoplastic diseases such as leukemia, and for the treatment of tumors such as breast cancer, cervical cancer and melanoma, to a host which needs such treatment. More specifically, the compounds of formula I as described above can be administered orally to a human in dosages that are in the range of about 0.1 to 100 μg per day for the treatment of neoplastic diseases such as leukemia, and for the treatment of tumors such as breast cancer, cervical cancer and melanoma.

The compounds of formula I as described above, can be administered orally in an effective amount, for the treatment of hyperproliferative skin diseases such as psoriasis, basal cell carcinomas, disorders of keratinization, and keratosis, to hosts which need such treatment. Preferably, the compounds of formula I as described above can be administered orally to a human in dosages that are in the range of about 0.001 to 100 μg per day for the treatment of hyperproliferative skin diseases such as psoriasis, basal cell carcinomas, disorders of keratinization, and keratosis.

The compounds of formula I, as described above, can be administered topically in an effective amount, for the treatment of hyperproliferative skin diseases such as psoriasis, basal cell carcinomas, disorders of keratinization, and keratosis, to hosts which need such treatment. Preferably, the compounds of formula I as described above can be administered topically to a human in dosages that are in the range of about 0.01 to about 100 μg per gram of topical formulation per day, for the treatment of hyperproliferative skin diseases such as psoriasis, basal cell carcinomas, disorders of keratinization, and keratosis.

The compounds of formula I, as described above, can be administered topically in an effective amount, for the treatment of sebaceous gland diseases, such as acne and seborrheic dermatitis, to a host in need of such treatment. Preferably, the compounds of formula I, as described above, can be administered topically to a human in dosages that are in the range of about 0.1 to about 1000 μg per gram of topical formulation per day, for the treatment of sebaceous gland diseases, such as, acne and seborrheic dermatitis.

The compounds of formula I as described above, can be administered orally in an effective amount, for the treatment of sebaceous gland diseases such as acne and seborrheic dermatitis to a host requiring such treatment. Preferably, the compounds of formula I, as described above, can be administered orally to a human in dosages that are in the range of about 0.07 μg to 770 μg per day, more preferably in the range of about 0.7 μg to 70 μg per day for the treatment of sebaceous gland diseases, such as acne.

The useful activity of compounds of formula I as agents for the treatment of tumors, particularly breast tumors, can be demonstrated by the following test procedures which are known in the art.

TETRAZOLIUM BASED MTT ASSAY

Cells:

T47-D (breast ductal carcinoma) were grown in RPMI-1640 medium supplemented with 10 μg/ml bovine insulin and 10% fetal bovine serum (FBS).

MCF-7 (breast adenocarcinoma) were grown in MEM (Eagle) supplemented with non-essential amino acids, 1 mM sodium pyruvate, 10 g/ml bovine insulin and 10% FBS Culture Conditions:

Cells were grown in appropriate medium to late log phase (about 80% confluency). T47-D or MCF-7 cells were then trypsinized and seeded at 4,000 or 2,000 cells/well, respectively.

Tetrazolium Based MTT Assay:

At 24 hours post seeding, serial dilutions of ethanol-solubilized drugs are prepared in the same medium and added to triplicate wells at a final concentration of 1,000 to 0.1 nM and 0.1% ethanol. On days 3 to 7 post drug addition, 50 μl of a 5 mg/ml MTT solution (3-(4,5-dimethylthiazol-2-yl)-2,5-diphenyl tetrazolium bromide in phosphate-buffered saline) is added to each well and incubation is continued at 37° C. for 2.5 hours. The plates are then spun briefly by centrifugation at 800 xg for 5 minutes, medium is aspirated from wells, and 50 μl ETOH/well is added to dissolve the formazan formed during the incubation period with MTT. After a 15 minute shaking, the optical density is determined for each well in an automatic plate reader at 570 and 660 nm. Percent inhibition of cell growth is calculated by comparing optical densities of cells treated with test compounds to those of cells treated only with 0.1% ethanol. $IC_{50}$ values are determined based on the Reed and Muench formula (Am. J. Hyg. 27:493-497 1938) and the results of two independent experiments are presented below:

TABLE I

| Test compound | $IC_{50}$ value (nM) | | |
|---|---|---|---|
| | T47-D cells Exp. 1* | T47-D cells Exp. 2 | MCF-7 cells Exp. 2 |
| 1,25-dihydroxy-16-ene-23 yne-26,27-hexafluoro-cholecalciferol | 0.63 | 0.95 | 0.42 |
| 1α,25-dihydroxy-16,23E-diene-26,27-hexafluoro-cholecalciferol | <0.1 | 0.9 | 0.05 |
| 1α,25-dihydroxy-16,23E-diene-19-nor-26,27-hexa-fluoro-cholecalciferol | 0.26 | 2.2 | 0.15 |
| 1α-fluoro-25-hydroxy-16,23E-diene-26,27-hexafluoro-cholecalciferol | — | — | 0.38 |

*Experiment 1 did not include MCF-7 cells.

The data show antiproliferative activity of the test compounds in human breast carcinoma cell lines.

The useful activity of compounds of formula I as agents for the treatment of hyperproliferative skin diseases can be demonstrated by the following test procedures which are known in the art, and which are also set forth in Holick et al., The Society for Investigative Dermatology, p. 708-714(1986).

Human Keratinocyte Antiproliferative Assay

Cells:

Primary or passage 1 subconfluent cultures of human neonatal keratinocytes were grown in Keratinocyte Growth Media ® (KGM ® modified MCDB 153, Clonetics, Inc. Catalog #CC3001) supplemented with antibiotics or calcium chloride as needed. Cultures were obtained from neonatal foreskin epithelial keratinocytes using standard procedures.

Culture Conditions:

Human neonatal foreskins were collected by circumcision and placed into tubes containing Dulbecco's minimum essential Media (DMEM) with 10% serum. Upon arrival at the laboratory, they were mechanically trimmed of excess dermis, and treated with a solution of trypsin/ethylenediamine tetraacetic acid (EDTA) (0.05%/0.02%) at 4° C. overnight. The epidermis was stripped from the dermis, agitated in buffered saline to remove basal keratinocytes and the stratum corneum later removed. The separated cells were centrifuged, resuspended in media, counted, and the cells plated onto plastic culture dishes or plates at 2,500 cells/cm² in KGM media according to protocols developed by Boyce and Ham, *In Vitro Models for Cancer Research* III, 246–274, (1986) for MCDB 153 media. The cultures are incubated in humidified chambers with 5% $CO_2$ at 37° C. with refeeding fresh media 2 to 3 times per week. Prior to reaching confluency, the cells are replated (called passage 1) at 25,000 cells/well on 6-well cluster plates (Costar catalog #3506) in KGM.

Antiproliferation Assay Protocol:

Approximately twenty-four hours after passage, the cells were refed with fresh KGM media supplemented to 1.5 mM $CaCl_2$ that contains test compound or vehicle. Solutions of test compounds were prepared as follows: 1 milligram quantities were received in amber glass vials and stored at −20° C. Sufficient 100% ethanol was added directly to vials to obtain a millimolar solution that was subsequently aliquoted into small amber vials, overlayed with argon gas and stored at −20° C. Each stock solution was thawed once, used and discarded. Stock solutions were used within 4 to 6 weeks. Aliquots from the stock solution were diluted directly into medium and then serially diluted from micromolar to picomolar concentrations. Compounds were typically tested at four concentrations in triplicate wells. Control wells are supplemented with vehicle alone at the highest concentration such as 0.1% ethanol. At the termination of the experiment prior to the cultures reaching confluency, the cells were enumerated by the following procedure. Dishes were washed with phosphate buffered saline, and then incubated with trypsin/EDTA solution for 30 minutes. Cells were suspended and an aliquot placed into isotonic buffered saline and counted on an electronic particle counter (Coulter Counter). The counter was periodically calibrated for the correct size of keratinocytes. Each well was counted in triplicate. The number of cell/dish was calculated according to dilution factors used and results are presented as percent inhibition from cell numbers obtained in control cultures. The results are set forth in Table II.

TABLE II

| Compound | Dose | Avg Cell No. | SEM[1] | % of Control | % SEM |
|---|---|---|---|---|---|
| 0.01% ETOH | Control | 4.88E+05 | 4.30E+04 | 100.00 | 8.81 |
| 1,25-dihydroxy-cholecalciferol | 10 nM | 4.60E+05 | 2.32E+04 | 94.26 | 5.04 |
| | 30 nM | 3.90E+05 | 1.46E+04 | 79.92 | 3.73 |
| | 100 nM | 3.12E+05 | 1.06E+04 | 63.98 | 3.40 |
| | 300 nM | 2.51E+05 | 1.54E+04 | 51.44 | 6.14 |
| | 1000 nM | 7.19E+05 | 4.34E+04 | 14.72 | 6.04 |
| 1α,25-dihydroxy-16,23E-diene-26,27-hexafluoro-cholecalciferol | 0.0001 nM | 4.57E+05 | 2.51E+04 | 93.65 | 5.48 |
| | 0.001 nM | 4.41E+05 | 1.86E+04 | 90.31 | 4.22 |
| | 0.01 nM | 5.42E+05 | 5.36E+04 | 110.95 | 9.91 |
| | 0.1 nM | 5.03E+05 | 1.65E+04 | 103.09 | 3.28 |
| | 1.0 nM | 2.87E+05 | 9.91E+04 | 58.71 | 3.46 |
| | 10 nM | 2.29E+05 | 1.60E+04 | 46.95 | 6.98 |
| | 100 nM | 2.03E+05 | 9.50E+04 | 41.62 | 4.68 |
| | 1000 nM | 3.04E+05 | 4.56E+04 | 6.23 | 14.98 |

[1] Standard error of the mean.
1,25-dihydroxy-cholecalciferol exhibited an average $ED_{50}$ (Dose that would obtain 50% of the number of cells as compared to the control) = 300 nM
1α,25-dihydroxy-16,23E-diene-26,27-hexafluoro-cholecalciferol exhibited an average $ED_{50}$ of 2 nM The useful activity of compounds of formula I as agents for the treatment of neoplastic diseases, such as leukemia, can be demonstrated by the following test procedures.

HL-60 Differentiation Assay:

The HL-60 tumor cell line was originally derived from a patient with promyleocytic leukemia and purchased from American Type Culture Collection (ATCC CCL240). The cells are maintained in suspension using the media RPMI 1640 (Gibco catalog #320-1875) supplemented with glutamine, antibiotics and 20% heat inactivated fetal bovine serum (FBS). For experimentation, cells were seeded at $0.9 \times 10^6$ cells per 25 cm$^2$ flask in medium supplemented with 0.25 mM sodium ascorbate. Compounds were added for a total of four days and were typically tested at five concentrations in duplicate flasks. All compounds were handled in the following manner. Stock solutions were made of $10^{-3}$M solutions in ethanol and stored in amber vials overlaid with argon at $-20°$ C. Stock solutions were diluted into medium at concentrations indicated. All flasks were supplemented with vehicle at a concentration of 0.1% ethanol. Control flasks were supplemented with vehicle alone at a concentration of 0.1% ethanol. Flasks were incubated upright for 4 days in 5% $CO_2$ at $37°$ C. On day 4, a 1 ml aliquot of cells was removed from the flasks, centrifuged for about 10 minutes, the media removed and the cells resuspended in a 0.2 ml of solution of nitroblue tetrazolium/phorbol 12 myristate 13-acetate (NBT/TPA) in media prepared on the day of enumeration as follows. Nitroblue tetrazolium was dissolved in media at 1 mg/ml. To this solution was added TPA to a final concentration of 100 ng/ml. This solution was kept in a covered vial on ice. The cells were suspended and incubated at $37°$ C. for 30 min. prior to transferring to ice. An aliquot was removed and the cells are counted using a hemocytometer. Cells without pigmented granules are judged to be undifferentiated while those containing blue black formazan (indicating conversion of NBT) granules were scored as differentiated. Results are expressed as percent differentiated cells by calculating the ratio of the number of dark cells per total number of cells counted. The results are set forth below in Table III.

TABLE III

| Compound | Dose | Percent Positive Cells | Approximate $ED_{50}$ |
|---|---|---|---|
| Control 0.01% ETOH | | 3.0 | |
| 1,25-dihydroxy-cholecalciferol | 0.1 nM | 2.0 | 25 nM |
| | 0.3 nM | 5.0 | |
| | 1.0 nM | 3.5 | |
| | 10.0 nM | 26.0 | |
| | 100.0 nM | 84.0 | |
| 1α,25-dihydroxy-16,23E-diene-26,27-hexafluoro-cholecalciferol | 0.1 nM | 6.0 | 0.6 nM |
| | 0.3 nM | 30.5 | |
| | 1.0 nM | 63.0 | |
| | 10.0 nM | 79.0 | |
| | 100.0 nM | 89.5 | |

The useful activity of compounds of formula I as agents for the treatment of sebaceous gland diseases, such as acne and seborrheic dermatitis, can be demonstrated by the following test procedure.

Sebaceous cells were isolated from adult human sebaceous glands, derived from facial skin removed during cosmetic surgery. This method is described in an article by Doran et al. in *J. Invest. Dermatol.* 96:341-348 (1991).

The cells were cultured in Iscove's medium containing 10% fetal calf serum and 4 μg/ml dexamethasone on a layer of growth-arrested 3T3 mouse fibroblasts.

Cells were plated in medium without the test compound and then given the compound in fresh medium 24-48 hours after the initial plating. The cultures were given fresh medium, containing the test compound, every 48 hours. On the day of harvesting, the cultures were rinsed with 0.03% ethylenediamine tetraacetic acid (EDTA) in phosphate buffered saline (PBS), to remove only the 3T3 fibroblasts. The remaining sebocyte colonies were incubated in 0.05% trypsin/0.03% EDTA to create a single cell suspension of sebocytes. The cells were diluted, mixed vigorously to maintain a single cell suspension, and counted in a hemocytometer.

All compounds were handled in the following manner. Stock solutions were made up as $10^{-2}$M solutions in degassed 100% ethanol and stored at $-20°$ C. in the dark. Solutions were never used after storage of more than a month. During experimental use the solutions, which had been aliquoted, were thawed once and used by diluting directly into complete medium to the appropriate concentration.

The compounds were tested for the inhibition of proliferation of sebaceous cells in vitro at the following concentrations: $10^{-9}$, $10^{-8}$, $10^{-7}$ and $10^{-6}$M.

The results are summarized in Table IV below as the amount of compound necessary to inhibit the proliferation of the sebaceous cells by 50% ($ED_{50}$) in μM as compared to a control, vehicle treated only, culture.

TABLE IV

| Compound | $ED_{50}$ (μM) |
|---|---|
| 1,25-dihydroxycholecalciferol | 0.05 |
| 1α,25-dihydroxy-16,23E-diene-26,27-hexafluorocholecalciferol | <0.001 |

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate, a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, adsorbable, water-soluble and emulsion-type bases such as petrolatum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or andydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials. In addition to application to the skin, the topical compositions of this invention can also be employed in the treatment of inflammations of mucous membranes, where such membranes are accessible to topical application of medication. For example, the topical composition can be applied to the mucous lining of the mouth or lower colon.

EXAMPLE 1

[3aR-[1(R*),3aα,4β7aβ]]-3,3a,5,6,7,7a-Hexahydro-7a-methyl-1-[6,6,6-trifluoro-5-hydroxy-1-methyl-5(trifluoromethyl)-3E-hexenyl]-4H-inden-4-ol In a dried 100 ml two neck round bottom flask was placed 148 mg (3.9 mmol) of lithium aluminum hydride and 6 ml of andydrous tetrahydrofuran. To this stirred suspension was added 211 mg (3.9 mmol) of sodium methoxide slowly under argon. The resulting mixture was cooled in an ice bath to 0° C., and then a solution of 300 mg (0.78 mmol) of [3aR-[1(R*),3aα,4β,7aβ]]-3,3a,5,6,7,7a-hexahydro-7a-methyl-1-[6,6,6-trifluoro-5-hydroxy-1-methyl-5(trifluoromethyl)-3-hexynyl]-4H-inden-4-ol in 10 ml of tetrahydrofuran was added dropwise. After the addition was completed, the reaction mixture was heated at reflux (oil bath at 80° C.) for 2 and ¾ hours, that was followed by stirring overnight at room temperature. After the addition of 5 ml of ether, the reaction mixture was cooled in an ice batch and hydrolyzed cautiously by the addition of 0.5 ml of water and 0.5 ml of 10% sodium hydroxide solution. After warm-up to room temperature, crystalline sodium sulfate and magnesium sulfate were added and the reaction mixture was filtered and the solid on the filter was washed with ethyl acetate. The combined filtrates were evaporated to dryness to give 329 mg of crude product. Purification was performed by flash chromatography on a 30 mm×6" silica gel column with hexane-ethyl acetate 3:1. It gave 275 mg (90%) of the title compound. $^1$H-NMR (CDCl$_3$): δ0.98 (d, J=6 Hz, 3H), 0.99 (s, 3H), 4.17 (s, 1H), 5.33 (bs, 1H), 5.57 (d, J=16 Hz, 1H), 6.22 (dt, J=7 and 16 Hz, 1H).

EXAMPLE 2

[3aR-[1(R*),3aα,7aβ]]-3,3a,5,6,7,7a-Hexahydro-7a-methyl-1-[6,6,6-trifluoro-5-hydroxy-1-methyl-5(trifluoromethyl)-3E-hexenyl]-4H-inden-4-one A solution of 267 mg (0.691 mmol) of [3aR-[1(R*),3aα,4β,7aβ]]-3,3a,5,6,7,7a-hexahydro-7a-methyl-1-[6,6,6-trifluoro-5-hydroxy-1-methyl-5(trifluoromethyl)-3E-hexynyl]-4H-inden-4-ol in 8 ml andydrous methylene chloride was treated with 830 mg (2.21 mmol) of pyridinium dichromate and 42 mg of pyridinium-p-toluenesulfonate. The brown mixture was stirred at room temperature for 2 hours, then additional 260 mg (0.691 mmol) of pyridinium dichromate and 13 mg of pyridinium-p-toluenesulfonate was added and the reaction on mixture was stirred for 1 and ½ hours more. At that time 20 ml of ether was added and the mixture was stirred for 20 minutes, filtered over celite and the solid on the filter was washed with 3×50 ml of ether. The combined filtrates were washed with ice-cold 40 ml 1N HCl, water, 50 ml 2N KHCO$_3$ and three times with water-brine. The aqueous layers were back-washed with 2×100 ml ether-ethyl acetate 1:1. The organic layers were dried over Na$_2$SO$_4$ and evaporated, to give 261 mg of crude product. Purification was done by flash chromatography on a 30 mm/6" column of silica gel with hexane-ethyl acetate 3:1 to give 233 mg (87%) of the title compound. $^1$H-NMR(CDCl$_3$): δ0.80(s,3H), 1.08 (d, J=6 Hz, 3H), 2.84 (dd, J=6 and 11 Hz, 1H), 5.32 (bs, 1H), 5.58 (d, J=16 Hz, 1H), 6.22 (dt, J=7 and 16 Hz, 1H).

EXAMPLE 3

[3aR-[1(R*),3aα,7aβ]]-3,3a,5,6,7,7a-Hexahydro-7a-methyl-1-[6,6,6-trifluoro-5-trimethylsilyloxy-1-methyl-5(trifluoromethyl)-3E-hexenyl]-4H-inden-4-one A solution of 426 mg (1.11 mmol) of [3aR-[1(R*),3aα,7aβ]]-3,3a,5,6,7,7a-hexahydro-7a-methyl-1-[6,6,6-trifluoro-5-hydroxy-1-methyl-5(trifluoromethyl)-3E-hexenyl]-4H-inden-4-one in 8 ml of anhydrous methylene chloride was treated with 1.2 ml (8.18 mmol) of trimethylsilyl imidazole. The solution was stirred at room temperature for 17 hours, under argon. 5 ml of water was added and stirred for 20 minutes, and then extracted with 3×90 ml of ethyl acetate. The organic layer was washed with water-brine, dried over Na$_2$SO$_4$, and evaporated to dryness. 490 mg of the crude product was purified by flash chromatography on a 30 mm/6" column of silica gel with hexane-ethyl acetate 12:1, to give 462 mg (90%) of the title compound.

EXAMPLE 4

1,25-Dihydroxy-16,23E-diene-26,27-hexafluorocholecalciferol

A solution of 2.04 g (3.5 mmol) of [3S-(3a,5β,Z)]-2-[2-[2-methylene-3,5-bis[[(1,1-dimethylethyl)dimethylsilyl]oxy]cyclohexylidene]ethyl]diphenyl phospine oxide in 20 ml of andydrous tetrahydrofuran was cooled in a dry ice bath to −78° C., to which was added 2.19 ml (3.5 mmol) of n-butyl lithium as 1.6M solution in hexane dropwise under argon. After stirring for 5 minutes, 540 mg (1.40 mmol) of [3aR-[1(R*),3aα,7aβ]]-3,3a,5,6,7,7a-hexahydro-7a-methyl-1-[6,6,6-trifluoro-5hydroxy-1-methyl-5(trifluoromethyl)-3E-hexeny]-4H-inden-4-one in 7 ml of tetrahydrofuran was added dropwise over 10 minutes, and the reaction mixture was stirred for two hours. After the addition of 15 ml of a 1:1 mixture of 2N Rochelle salt and 2N KHCO$_3$ solution, the reaction was let to come to room temperature. After another 30 ml of Rochelle salt/KHCO$_3$ mixture was added, it was extracted with 3×100 ml of ethyl acetate. The organic layer was washed three times with brine, dried over Na$_2$SO$_4$ and evaporated to dryness. 2.4 g of crude product was purified by flash chromatography on a 50 mm/7" column of silica gel with hexane-ethyl acetate (8:1) to give 410 mg of 1,3 disilyloxy intermediate. To the solution of this intermediate in 5 ml andydrous tetrahydrofuran was added 4.5 ml (4.5 mmol) of 1N tetrabutylammonium fluoride in tetrahydrofuran under argon and stirred for 18 hours at room temperature. After additional 2.5 ml of tetrabutylammonium fluoride was added, the stirring was continued for 22 hours. 5 ml of water was added, stirred 20 minutes, 25 ml of brine was added and extracted with 3×100 ml ethyl acetate. The organic layer was washed four times with water-brine, dried over Na$_2$SO$_4$ and evaporated to dryness to give 354 mg of crude product. Purification by flash chromatography on a 30 mm/6" column of silica gel with hexane-ethyl acetate (1:3) gave 270 mg (37%) of the title compound as white foam. $[\alpha]_D^{25}$ +24° (c0.2%, EtOH); UVλ$_{max}$ (EtOH): 204 nm (ε18200), 262–263 nm (ε15900); 1H-NMR (CDCl$_3$): δ0.68 (s, 3H), 1.04 (d, J=6.5 Hz, 3H), 2.61 (dd, J=3 and 13 Hz, 1H), 2.83 (dd, J=4.5 and 12 Hz, 1H), 4.24 (bs, 1H), 4.45 (bs, 1H), 5.02 (s, 1H), 5.34 (bs, 2H), 5.58 (d, J=15.5 Hz, 1H), 6.11 (d, J=11.5 Hz, 1H), 6.23 (dt, J=7 and 15.5 Hz, 1H), 6.37 (d, J=11.5 Hz, 1H).

Analysis: Calcd for C$_{27}$H$_{34}$F$_6$O$_3$: C 62.30, H 6.58; Found: C 62.55, H 6.70.

EXAMPLE 5

25-hydroxy-16,23E-diene-26,27-hexafluorocholecalciferol

The title compound can be obtained by the same procedure described in the Example 4 when [3S-(3α,5β,Z)]-2-[2-[2-methylene-5-[[(1,1-dimethylethyl)dimethylsilyl]oxy]cyclohexylidene]ethyl]diphenyl phosphine oxide is used as the A-ring precursor instead of [3S-(3α,5β,Z)]-2-[2-[2-methylene-3,5-bis[[(1,1-dimethylethyl)dimethylsilyl]oxy]cyclohexylidene]ethyl]diphenyl phosphine oxide.

EXAMPLE 6

1α-Fluoro-25-hydroxy-16,23E-diene-26,27-hexafluorocholecalciferol

A solution of 490 mg (1.04 mmol) of [3S-(3α,5β,Z)]-2-[2-[2-methylene-3-fluoro-5-[[(1,1-dimethylethyl)dimethylsilyl]oxy]cyclohexylidene]ethyl]diphenyl phosphine oxide in 6 ml of andydrous tetrahydrofuran was cooled in dry ice bath to −78° C., and then was added 0.65 ml (1.04 mmol) of n-butyllithium as 1.6M solution in hexane dropwise under argon. After stirring for 5 minutes, a solution of 290 mg (0.635 mmol) of [3aR-[R*),3aα,7aβ]]-3,3a,5,6,7,7a-hexahydro-7a-methyl-1-[6,6,6-trifluoro-5-trimethylsilyloxy-1-methyl-5(trifluoromethyl)-3E-hexenyl]-4H-inden-4-one in 4.5 ml of anhydrous tetrahydrofuran was added dropwise over a ten-minute period. The reaction mixture was stirred for one hour and 50 minutes at −78° C., and then quenched by the addition of 10 ml of a 1:1 mixture of 2N Rochelle salt and 2N KHCO$_3$ solutions. After the warm-up to room temperature, additional 30 ml of the Rochelle salt/KHCO$_3$ were added, and extracted with 3×100 ml ethyl acetate. The organic layers were washed with brine, dried over Na$_2$SO$_4$, and evaporated to dryness. 688 mg of crude product was purified by flash chromatography on a 40 mm/6" column of silica gel with hexane-ethyl acetate 20:1, to give 260 mg of amorphous disilylated intermediate.

To the solution of 260 mg of disilylated intermediate in 4 ml of andydrous tetrahydrofuran was added 3.5 ml (3.5 mmol) of a 1M tetrabutylammonium fluoride in tetrahydrofuran under argon. The resulting solution was stirred at room temperature for 23 hours. After the addition of 5 ml of water, and stirring for 20 minutes, 25 ml of brine was added and the mixture was extracted with 3×90 ml of ethyl acetate. The organic layers were washed with water-brine, dried over Na$_2$SO$_4$ and evaporated to dryness. 232 mg of crude product was purified by flash chromatography on a 30 mm/6" column of silica gel with hexane-ethyl acetate 2:1, and HPLC on a YMC 50 mm/50 cm silica column with hexane-ethyl acetate 3:2, to give 140 mg (42%) of amorphous title compound. $[\alpha]_D^{25}$ +22° (c0.2,EtOH);UV(EtOH)-λ$_{max}$:241 nm (ε13600), 267/268 nm(ε13350); 1H-NMR (CDCl$_3$): δ0.69 (s, 3H), 1.04 (d, J=6.5 Hz, 3H), 2.63 (dd, J=3 and 13.5 Hz, 1H), 4.23 (bs, 1H), 5.12 (s, 1H), 5.16 (ddd, J=50, 5 and 7 Hz, 1H), 5.34 (s, 1H), 5.41 (s, 1H), 5.58 (d, J=15.5 Hz, 1H), 6.12 (d, J=11.5 Hz, 1H), 6.23 (dt, J=15.5 and 7 Hz, 1H), 6.40 (d, J=11.5 Hz, 1H).

Analysis: Calcd for C$_{27}$H$_{33}$F$_7$O$_2$: C 62.06, H 6.37; Found: C 61.59, H 5.89.

EXAMPLE 7

1,25-Dihydroxy-16,23E-diene-26,27-hexafluoro-19-nor-cholecalciferol

A solution of 854 mg (1.5 mmol) of [3R-(3α,5β,Z)-3,5-bis[[(1,1-dimethylethyl)dimethylsilyl]oxy]cyclohexylidene]ethyl]diphenyl phosphine oxide in 9 ml of andydrous tetrahydrofuran was cooled in a dry ice bath to −78° C. and was then treated with 0.937 ml (1.5 mmol) of n-butyllithium as a 1.6M solution in hexane, dropwise under argon. After stirring for 5 minutes, the reaction mixture was treated with a solution of 414 mg (0.907 mmol) of [3aR-[1(R*),3aα,7aβ]]-3,3a,5,6,7,7a-hexahydro-7a-methyl-1-[6,6,6-trifluoro-5-trimethylsilyloxy-1-methyl-5(trifluoromethyl)-3E-hexenyl]-4H-inden-4-one in 5 ml of anhydrous tetrahydrofuran, dropwise over 10 minutes. The reaction mixture was then stirred at −78° C. for one hour and 45 minutes, quenched by the addition of 15 ml of 1:1 mixture of 2N Rochelle salt and 2N KHCO$_3$ solutions and allowed to warm up to room temperature. Additional 30 ml of the Rochelle salt/KHCO$_3$ mixture was added and extracted with 3×100 ml ethyl acetate. The organic layers were washed three times with brine, dried over Na$_2$SO$_4$ and evaporated to dryness. 1.09 g of crude product was purified by flash chromatography on a 40 mm/6" column of silica gel with hexane-ethyl acetate 1:3 to give 430 mg of trisilylated intermediate.

To the solution of this intermediate in 4.5 ml of andydrous tetrahydrofuran was added 4.5 ml (4.5 mmol) of a 1M tetrabutylammonium fluoride in andydrous tetrahydrofuran under argon. After stirring 24 hours at room temperature, an additional 2.5 ml of tetrabutylammonium fluoride was added, and the reaction was stirred 23 hours. 5 ml water was added, stirred 20 minutes, 25 ml brine was added and extracted with 3×100 ml ethyl acetate. The organic layers were washed four times with a water-brine mixture, dried over $Na_2SO_4$ and evaporated to dryness. 350 mg of the crude product was purified by flash chromatography on a 30 mm/6" column of silica gel with hexane-ethyl acetate 1:4, and by HPLC on a YMC 50 mm/50 cm silica column with hexane-ethylacetate 1:8. It gave 260 mg (56%) of amorphous title compound; $[\alpha]^{D25}+23.5°$ (c 2,EtOH); UV-(EtOH)$\lambda_{max}$:sh234/235 nm($\epsilon$20,600); 242 nm($\epsilon$29,100), 250/251 nm($\epsilon$34,100), 260 nm($\epsilon$22,750); $^1$H-NMR(CDCl$_3$): $\delta$0.68(s,3H), 1.05(d, J=6.5 Hz, 3H), 2.49(dd, J=2 and 12 Hz,1H), 2.77(J=3 and 12 Hz, 1H), 2.80(dd, J=4 and 12 Hz, 1H), 4.06 (m, 1H), 4.13(m, 1H), 5.35(s, 1H), 5.58(d, J=16 Hz, 1H), 5.95 (f, J=11 Hz, 1H), 6.23(dt, J=7 and 16 Hz, 1H), 6.31 (d, J=11 Hz, 1H).

EXAMPLE 8

[3aR-[1(R*),3a$\alpha$,4$\beta$,7a$\beta$]]-3,3a,5,6,7,7a-Hexahydro-7a-methyl-1-[6,6,6-trifluoro-5-hydroxy-1-methyl-5-(trifluoromethyl )-3Z-hexenyl]-4H-inden-4-ol A mixture of 1.6 g (4.16 mmol) of [3aR-[1(R*),3a$\alpha$,4$\beta$,7a$\beta$]]-3,3a,5,6,7,7a-hexahydro-7a-methyl-1-[6,6,6-trifluoro-5-hydroxy-1-methyl-5-(trifluoromethyl)-3-hexynyl]-4H-inden-4-ol, 16 ml ethylacetate, 40 ml hexane, 1.6 ml absolute ethanol, 80 μl quinoline and 320 mg Lindlar catalyst was stirred under hydrogen atmosphere at room temperature for 70 min. The reaction mixture was filtered over Celite and washed with 3×70 ml ethyl acetate. The filtrate was washed with 25 ml 1N HCl and a mixture of water and brine. The aqueous layers were extracted with 2×90 ml ethyl acetate, and the combined organic layers were dried over $Na_2SO_4$ and evaporated to dryness to give 1.72 g of crude product. This crude product was purified by flash chromatography on a silica gel column and HPLC with hexane-ethyl acetate 3:1, to give 1.58 (99%) of amorphous title compound.

EXAMPLE 9

[3aR-[1(R*),3a$\alpha$,7a$\beta$]]-3,3a,5,6,7,7a-Hexahydro-7a-methyl-1-[6,6,6-trifluoro-5-hydroxy-1-methyl-5-(trifluoromethyl)-3Z-hexenyl]-4H-inden-4-one Using the same procedure as described in Example 2, but starting with [3aR-[1(R*),3a$\alpha$,4$\beta$,7a$\beta$]]-3,3a,5,6,7,7a-hexahydro-7a-methyl-1-[6,6,6-trifluoro-5-hydroxy-1-methyl-5-(trifluoromethyl)-3Z-hexenyl]-4H-inden-4-ol instead the corresponding trans analog, the oxidation gave the title compound in 92% yield as an amorphous solid.

EXAMPLE 10

[3aR-[1(R*),3a$\alpha$,7a$\beta$]]-3,3a,5,6,7,7a-Hexahydro-7a-methyl-1-[6,6,6-trifluoro-5-trimethylsilyloxy-1-methyl-5-(trifluoromethyl)-3Z-hexenyl]-4H-inden-4-one Using the same procedure as described in example 3, but starting with [3aR-[1(R*),3a$\alpha$,7a$\beta$]]-3,3a,5,6,7,7a-hexahydro-7a-methyl-1-[6,6,6-trifluoro-5-hydroxy-1-methyl-5-(trifluoromethyl)-3Z-hexenyl]-4H-inden-4-one instead the corresponding trans analog, the reaction gave the title compound in 96% yield as an amorphous solid.

EXAMPLE 11

1,25-Dihydroxy-16,23Z-diene-26,27-hexafluoro-19-norcholecalciferol

Using the same procedure as described in the example 7, but starting with [3aR-[1(R*),3a$\alpha$,7a$\beta$]]-3,3a,5,6,7,7a-hexahydro-7a-methyl-1-[6,6,6-trifluoro-5-trimethylsilyloxy-1-methyl-5-(trifluoromethyl)-3Z-hexenyl]-4H-inden-4-one instead the corresponding trans analog, the reaction sequence gave the title compound.

EXAMPLE 12

1,25-Dihydroxy-16,23Z-diene-26,27-hexafluorocholecalciferol

A solution of 552 mg (0.947 mmol) of [3S(3$\alpha$,5$\beta$,Z)]-2-[2-[2-methylene-3,5-bis[[(1,1-dimethylethyl)dimethylsilyl]oxy]cyclohexylidene]ethyl]diphenyl phosphine oxide in 6 ml of andydrous tetrahydrofuran was cooled to −78° C. and treated with 0.578 ml (0.925 mmol) of a 1.6M solution of n-butyl lithium in hexane dropwise under argon. After stirring for a few minutes, the red solution was treated with a solution of 256 mg (0.561 mmol) of [3aR-[1(R*),3a$\alpha$,7a$\beta$]]-3,3a,5,6,7,7a-hexahydro-7a-methyl-1-[6,6,6-trifluoro-5-trimethylsilyloxy-1-methyl-5-(trifluoromethyl)-3Z-hexenyl]-4H-inden-4-one in 4.5 ml of anhydrous tetrahydrofuran dropwise over a 10 minute period. The reaction was stirred at −78° C. for 90 minutes and then quenched by addition of 10 ml of a 1:1 mixture of 2N Rochelle salt and 2N KHCO$_3$ solutions and allowed to warm up to room temperature. After addition of 25 ml more of the Rochelle salt/KHCO$_3$ solution, the mixture was extracted with 3×120 ml ethyl acetate.

The organic layers were washed three times with water-brine mixture, dried over $Na_2SO_4$ and evaporated to dryness to give 690 mg of crude product. This crude product was purified by flash chromatography on a silica gel column with hexane-ethyl acetate 20:1 to give 335 mg of silylated title compound.

A solution of 335 mg (0.408 mmol) of the silylated intermediate in 6 ml of andydrous tetrahydrofuran was treated with 3.7 ml (3.7 mmol) of a 1M solution of tetrabutyl ammonium fluoride in tetrahydrofuran. The reaction mixture was stirred at room temperature for 22½ hours under argon. It was then quenched with 5 ml of water, stirred for 30 minutes, and after evaporation of tetrahydrofuran and addition of 10 ml of water extracted with 3×90 ml ethyl acetate. The organic layers were washed four times with a water-brine mixture, dried over $Na_2SO_4$ and evaporated. The crude product (273 mg) was purified by flash chromatography on a silica gel column with hexane-ethyl acetate 1:2.5 to give 206 mg (70.5%) of title compound. $[\alpha]_D^{25}+23.5°$ (c 0.2%, EtOH); UV(EtOH) $\lambda$ max: 206 nm ($\epsilon$16720), 263 nm ($\epsilon$14690); $^1$H-NMR (CDCl$_3$): $\delta$0.68(s, 3H), 1.06 (d, J=6.9 Hz, 3H), 4.24 (brm, 1H), 4.45 (brm, 1H), 5.01 (s, 1H), 5.34 (s, 1H), 5.42 (d,J=12.5 Hz, 1H), 5.97 (dt, J=12.5 and 7 Hz, 1H), 6.11 (d,J=11.4 Hz, 1H), 6.38 (d,J=11.4 Hz, 1H).

EXAMPLE 13

25-Hydroxy-16,23Z-diene-26,27-hexafluorocholecalciferol

A solution of 452 mg (1 mmol) of [3S-(3α,5β,Z)]-2-[2-[2-methylene-5-[[(1,1-dimethylethyl)dimethylsilyl]oxy]-cyclohexylidene]ethyl]diphenyl phosphine oxide in 6 ml of andydrous tetrahydrofuran was cooled to −78° C. and treated with 0.625 ml (1 mmol) of a 1.6M solution of n-butyl lithium in hexane dropwise under argon. After stirring for 5 minutes, the solution was treated with a solution of 276 mg (0.605 mmol) of [3aR-[1(R*)-,3aα,7aβ]]-3,3a,5,6,7,7a-hexahydro-7a-methyl-1-[6,6,6-trifluoro-5-trimethylsilyloxy-1-methyl-5-(trifluoromethyl)-3Z-hexenyl]-4H-inden-4-one in 4 ml of andydrous tetrahydrofuran dropwise over a 10 minute period. The reaction mixture was stirred at −78° C. for 1¾ hours, and then quenched by addition of 10 ml of a 1:1 mixture of 2N Rochelle salt and 2N KHCO₃ solutions and allowed to warm up to room temperature. After addition of 30 ml more of the Rochelle salt/KHCO₃ solution, the resulting mixture was extracted with 3×100 ml ethyl acetate. The organic layers were washed three times with brine, dried over $Na_2SO_4$ and evaporated to dryness to give 598 mg of crude product. This crude product was purified by flash chromatography on a silica gel column with hexane-ethyl acetate 10:1 to give 364 mg of silylated title compound.

To a solution of 364 mg of silylated intermediate in 4.5 ml andydrous tetrahydrofuran was added 3.9 ml (3.9 mmol) of a 1M solution of tetrabutyl ammonium fluoride in tetrahydrofuran under argon. The resulting solution was stirred at room temperature for 18 hours, and then quenched with addition of 5 ml water and stirring for 15 minutes. After addition of 25 ml brine, the mixture was extracted with 3×100 ml of ethyl acetate. The organic layers were washed four times with the mixture of water and brine, dried over $Na_2SO_4$ and evaporated to dryness, to give 321 mg of crude product. This crude product was purified by flash chromatography on a silica gel column with hexane-ethyl acetate 5:2 and HPLC with hexane-ethyl acetate 2:1. It gave 228 mg (74.75%) of the title compound as an amorphous solid. UV(EtOH) λ max: 204/205 nm (ε19800), 263 nm (ε17600); ¹H-NMR (CDCl₃): δ0.68(s, 3H), 1.06 (d,J=6.9 Hz, 3H), 3.97 (brm, 1H), 4.83 (brm, 1H), 5.06 (s, 1H), 5.37 (s, 1H), 5.42 (d,J=12.1 Hz, 1H), 5.97 (dt, J=12.1 and 7 Hz, 1H), 6.13 (d,J=11 Hz, 1H), 6.23 (d,J=11 Hz, 1H)

EXAMPLE 14

| Oral Dosage Form Soft Gelatin Capsule | |
|---|---|
| | mg/Capsule |
| 25-hydroxy-16-23E-diene-26,27-hexafluorocholecalciferol | 0.0001–0.010 |
| Butylated Hydroxytoluene (BHT) | 0.016 |
| Butylated Hydroxyanisole (BHA) | 0.016 |
| Fractionated Coconut Oil (Neobee M-5) | 160.0 |

1. Suspend the Butylated Hydroxytoluene and Butylated Hydroxyanisole in fractionated coconut oil. Warm to about 50° C. and stir until dissolved.
2. Blanket the solution in step 1 with nitrogen and add 25-hydroxy-16,23E-diene-26,27-hexafluorocholecalciferol. Stir until 25-hydroxy-16,23E-diene-26,27-hexafluorocholecalciferol has dissolved, maintaining the nitrogen blanket.
3. Fill in soft gelatin capsules

EXAMPLE 15

| Topical Cream | |
|---|---|
| | mg/gm |
| 25-hydroxy-16-23E-diene-26,27-hexafluorocholecalciferol | 0.001–1.0 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. to 100 gm |

1. Melt the Cetyl Alcohol, Stearyl Alcohol, Sorbitan Monostearate, Glyceryl Monostearate and Polyoxyethylene Stearate Blend, Polysorbate 60, Mineral oil and a portion (60%) of Propylene Glycol together in a stainless steel container at 70° C. in a water bath.
2. Dissolve Butylated Hydroxyanisole and Propylparaben in the material from step 1 and maintain at 70°–72° C. Record the temperature of the melt.
3. Heat the Sorbitol Solution and the water in a suitable container at 70°–75° C.
4. Add the Edetate Disodium and Methylparaben to the solutions in step 3 and mix until dissolved. Record the temperature of the aqueous phase.
5. Dissolve the appropriate amount of 25-hydroxy-16,23E-diene-26,27-hexafluorocholecalciferol in another portion (30%) of the Propylene Glycol in a beaker and add this to the material from step 2 while mixing. Rinse the container with the remaining (10%) of the Propylene Glycol and add this to the mixture from step 2. Maintain a nitrogen atmosphere above the product during this and subsequent steps.
NOTE: Once 25-hydroxy-16,23E-diene-26,27-hexafluorocholecalciferol is added, steps 5 and 6 must be completed in rapid succession.
6. Add the oil phase from step 2 to the aqueous phase from step 5 while emulsifying with a high shear mixer. Rinse the oil phase container by withdrawing a portion of the emulsion and add this immediately to the rest of the emulsion.
7. Continue mixing and allow the product to cool to 50°–55° C. Remove an aliquot for determination of water content and droplet size. Record the result. Add additional water if necessary.
8. Continue mixing with a paddle mixer until the product cools to room temperature. Record the weight of the final product.
9. Transfer the cream to appropriate containers.
NOTE 1. The manufacturing has to be done in amber light. 2. The final cream should be packaged within 7 days from completion of its manufacture.

We claim:
1. A compound of the formula

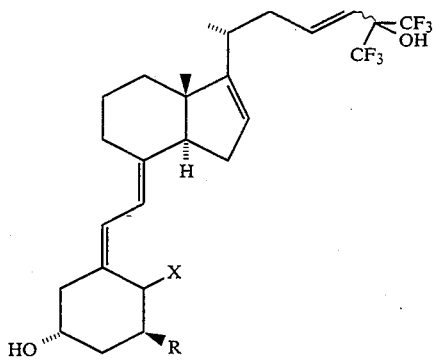

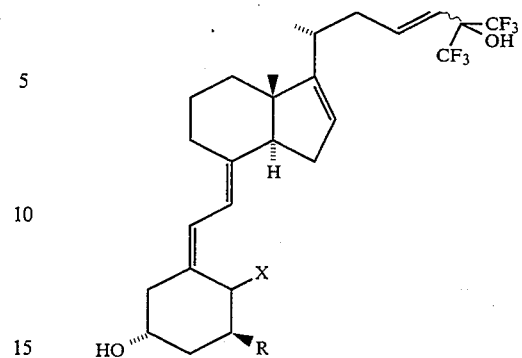

Wherein R is hydrogen, hydroxy, or fluorine, X is H₂ or =CH₂, and the 23,24-double bond is E or Z.

2. The compound in accordance with claim 1, wherein R is hydroxy or fluorine, and the 23,24-double bond is E.

3. The compound in accordance with claim 1, 26,26,26,27,27,27-hexafluoro-1α,25-dihydroxy-16,23E-diene-cholecalciferol.

4. The compound in accordance with claim 1, 26,26,26,27,27,27-hexafluoro-25-hydroxy-16,23E-diene-cholecalciferol.

5. The compound in accordance with claim 1, 26,26,26,27,27,27-hexafluoro-1α-fluoro-25-hydroxy-16,23E-diene-cholecalciferol.

6. The compound in accordance with claim 1, 26,26,26,27,27,27-hexafluoro-1α,25-dihydroxy-16,23E-diene-19-nor-cholecalciferol.

7. A pharmaceutical composition comprising an effective amount of a compound of the formula Wherein R is hydrogen, hydroxy or fluorine, X is H₂ or =CH₂ and the 23,24-double bond is E or Z, and an inert carrier.

8. The composition in accordance with claim 7, wherein R is hydroxy or fluorine, and the 23,24-double bond is E.

9. The composition in accordance with claim 7, wherein the compound of formula I is 26,26,26,27,27,27-hexafluorol-1α,25-dihydroxy-16,23E-diene-cholecalciferol 10. The composition in accordance with claim 7, wherein the compound of formula I is 26,26,26,27,27,27-hexafluoro-25-hydroxy-16,23E-diene-cholecalciferol.

11. The composition in accordance with claim 7, wherein the compound of formula I is 26,26,26,27,27,27-hexafluoro-1α-fluoro-25-hydroxy-16,23E-diene-cholecalciferol.

12. The composition in accordance with claim 7, wherein the compound of formula I is 26,26,26,27,27,27-hexafluoro-1,25-dihydroxy-16,23E-diene-19-nor-cholecalciferol.

13. The composition in accordance with claim 7, suitable for oral administration.

14. The composition in accordance with claim 7, suitable for topical administration.

* * * * *

UNITED STATES PATENT AND TRADEMARK OFFICE
CERTIFICATE OF CORRECTION

PATENT NO. : 5,428,029
DATED : June 27, 1995
INVENTOR(S) : Doran, et al.

It is certified that error appears in the above-indentified patent and that said Letters Patent is hereby corrected as shown below:

Column 11, line 12: "10 g/ml bovine" should read --- 10 µg/ml bovine --- .

Claim 9, Column 24, line 25: "hexafluorol" should read --- hexafluoro --- .

Signed and Sealed this

Thirty-first Day of October 1995

*Attest:*

BRUCE LEHMAN

*Attesting Officer*     *Commissioner of Patents and Trademarks*